(12) United States Patent
Moszner et al.

(10) Patent No.: US 10,342,744 B2
(45) Date of Patent: Jul. 9, 2019

(54) COMPOSITIONS WITH CONTROLLED NETWORK STRUCTURE

(71) Applicants: Ivoclar Vivadent AG, Schaan (LI); Technische Universität Wien, Vienna (AT)

(72) Inventors: Norbert Moszner, Mauren (LI); Urs-Karl Fischer, Arbon (CH); Iris Lamparth, Grabs (CH); Peter Burtscher, Rankweil (AT); Robert Liska, Schleinbach (AT); Christian Gorsche, Vienna (AT); Konstanze Seidler, Oberrohrbach (AT); Paul Gauss, Vienna (AT)

(73) Assignees: Ivoclar Vivadent AG, Schaan (LI); Technische Universität Wien, Vienna (AT)

( * ) Notice: Subject to any disclaimer, the term of this patent is extended or adjusted under 35 U.S.C. 154(b) by 7 days.

(21) Appl. No.: 15/325,246

(22) PCT Filed: Jul. 9, 2015

(86) PCT No.: PCT/EP2015/065771
§ 371 (c)(1),
(2) Date: Jan. 10, 2017

(87) PCT Pub. No.: WO2016/005534
PCT Pub. Date: Jan. 14, 2016

(65) Prior Publication Data
US 2017/0172855 A1    Jun. 22, 2017

(30) Foreign Application Priority Data

Jul. 11, 2014  (EP) .................... 14176729

(51) Int. Cl.
| | | |
|---|---|---|
| *A61K 6/00* | (2006.01) | |
| *A61K 6/08* | (2006.01) | |
| *A61K 6/083* | (2006.01) | |
| *C07C 317/28* | (2006.01) | |
| *C07C 317/44* | (2006.01) | |
| *C07C 323/52* | (2006.01) | |
| *C07F 9/40* | (2006.01) | |

(52) U.S. Cl.
CPC ............ *A61K 6/0052* (2013.01); *A61K 6/083* (2013.01); *C07C 317/28* (2013.01); *C07C 317/44* (2013.01); *C07C 323/52* (2013.01); *C07F 9/4015* (2013.01)

(58) Field of Classification Search
CPC ...... A61K 6/08; A61K 6/0052; C07C 317/28; C07C 317/44; C07C 323/52; C07F 9/1405
USPC ........ 523/105, 109, 113, 114, 115, 116, 117, 523/118
See application file for complete search history.

(56) References Cited

U.S. PATENT DOCUMENTS

| | | |
|---|---|---|
| 2,856,390 A | 10/1958 | Coover, Jr. et al. |
| 5,932,675 A | 8/1999 | Rizzardo et al. |
| 6,316,519 B1 | 11/2001 | Berge et al. |
| 8,404,758 B2 * | 3/2013 | Bowman .............. C08F 2/38 522/104 |
| 2012/0016052 A1 | 1/2012 | Bowman et al. |
| 2012/0295228 A1 | 11/2012 | Abuelyaman et al. |

OTHER PUBLICATIONS

Braga, Roberto R. et al., "Factors involved in the development of polymerization shrinkage stress in resin-composites: A systematic review," Academy of Dental Materials 21 (2005), 962-970. Published by Elsevier Ltd.
Stansbury, Jeffrey W., "Dimethacrylate network formation and polymer property evolution as determined by the selection of monomers and curing conditions," Academy of Dental Materials 28 (2012), 13-22. Published by Elsevier Ltd.
Mathias, Lon. J., "A novel thioether polymer with pendent ester groups from a readily available acrylate derivative," Polymer Bulletin 27 (1992), 395-398. Springer-Verlag.
Labuschagne, A. Johan H. et al., "New General Syntheses for Symmetrical and Unsymmetrical Organic Sulphides," Tetrahedron Letters No. 39, pp. 3571-3574, 1976. Pergamon Press, Great Britain.
Harvey, I. W., "Free Radical Addition Reactions of Allylic Sulfones to Alkenes," Tetrahedron, vol. 53, No. 18, pp. 6493-6508, 1997. Published by Elsevier Ltd. Great Britain.
Pudikova, A. A., et al., "Cascade Synthesis of New Aryl 2-Phenylallyl Sulfones from a-Methylstyrene and Aromatic Mono- and Bissulfonyl Chlorides," Russian Journal of Organic Chemistry, 2010, vol. 46, No. 3, pp. 352-354. Pleiades Publishing, Ltd., 2010.
Ezquerra, J. et al., "Efficient Synthesis of 4-Methylene-L-Glutamic Acid and its Cyclopropyl Analogue," Tetrahedron, vol. 5, No. 5, pp. 921-926, 1994. Published by Elsevier Science Ltd. Great Britain.
International Preliminary Report on Patentability of PCT/EP2015/065771, dated Jan. 17, 2017, 9 pages.

* cited by examiner

*Primary Examiner* — Sanza L. McClendon
(74) *Attorney, Agent, or Firm* — Ann M. Knab; Thad McMurray

(57) ABSTRACT

Radically polymerizable dental material, which contains at least one compound of Formula I:

$$A \left[ X \underset{CH_2}{\overset{R^1}{\diagdown\!\!\diagup\!\!\diagdown}} L \right]_n \qquad \text{Formula I}$$

The material preferably additionally contains a radically polymerizable monomer, an initiator for the radical polymerization and filler. It is characterized by a low polymerization contraction stress.

19 Claims, 1 Drawing Sheet

COMPOSITIONS WITH CONTROLLED NETWORK STRUCTURE

CROSS-REFERENCE TO RELATED APPLICATIONS

This application is a National Stage application of International patent application PCT/EP2015/065771 filed on Jul. 9, 2015, which claims priority to European patent application No. 14176729.3 filed on Jul. 11, 2014, the disclosures of which are incorporated herein by reference in their entirety.

The present invention relates to thermally curing and/or light-curing composites for preparing dental cements and filling composites for inlays, onlays, crowns, bridges or veneering materials.

Dental composites, which are used e.g. as composite cement or as direct filling material, inlay, onlay, crown or veneering material, contain a polymerizable organic matrix and one or more fillers, which are usually surface-modified with a polymerizable adhesion promoter. Depending on the type of fillers, the monomer matrix and the application, the fill level can vary between approx. 50 and 90 wt.-%, wherein cements have a lower fill level in comparison with filling composites.

As a rule, the polymerizable organic matrix contains a mixture of monomers, initiator components, stabilizers and pigments. Mixtures of dimethacrylates are usually used as resins. Examples of this are the highly viscous dimethacrylates 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) or the dimethacrylates of lower viscosity used as diluting monomers, such as e.g. bismethacryloyloxymethyltricyclo [5.2.1.]decane (TCDMA), decanediol-1,10-dimethacrylate ($D_3MA$) and triethylene glycol dimethacrylate (TEGDMA).

In the radical polymerization of dental composites, the polymerization shrinkage ($\Delta V_P$) of the monomers used results in a contraction in volume, which can lead to the very disadvantageous marginal gap formation in filling composites. In the polymerization of monofunctional methacrylates, such as e.g. MMA ($\Delta V_P$=21.0 vol.-%), the polymerization shrinkage does not lead to the build-up of a polymerization shrinkage stress (PCS), because the reduction in the volume can be compensated for by a simple flow of the macromolecules formed. In the case of the cross-linking polymerization of multifunctional methacrylates, however, a 3-dimensional polymer network already forms within a few seconds at the so-called gel point, i.e. already at a low monomer conversion, with the result that the polymerization shrinkage cannot be compensated for by viscous flow and a substantial PCS builds up in the material with increasing monomer conversion. The development of the PCS in filling composites is dependent on numerous factors, including the amount of volume contraction during the polymerization (curing or post-curing), the visco-elastic properties (elasticity modulus and modular organization, glass transition temperature ($T_G$) of monomer and polymer, viscosity and flow behaviour), the polymerization kinetics of the polymer network formation (resin functionality, cross-linking density, proportion of cyclic structures, polymerization rate, temperature, monomer and double-bond conversion), the type of curing and the type of restoration (layer thickness, cavity geometry). A particularly high PCS is observed in the case of light-curing (cf. R. R. Braga, R. Y. Ballester, J. L. Ferracane, Dent. Mater. 21 (2005) 962-970; J. W. Stansbury, Dent. Mater. 28 (2012) 13-22).

Numerous strategies were followed for reducing the PCS. This includes clinical methods, such as e.g. the incremental layer technique, the use of cavity lacquers with low elasticity modulus to form a stress-absorbing layer, the use of special illumination strategies (soft-start) or pre-heating the composites to improve the flow properties. The use of new, low shrinkage monomers, e.g. of monomers with ring-opening polymerizable groups, or the use of customized crosslinkers, e.g. with photo- or thermolabile spacers, can likewise lead to composites with low PCS.

Moreover, it was attempted to reduce the PCS through the addition of hyperbranched monomers, nanogels or nanotubes as well as of low-profile additives or expandable fillers.

WO 98/37104 discloses a method for controlling the molecular weight in the preparation of linear polymers by photo-initiated radical polymerization of vinyl monomers, in which the photoinitiator is used together with an addition-fragmentation chain transfer reagent.

U.S. Pat. No. 5,932,675 discloses a method for preparing polymers with low molecular weight by radical polymerization. The molecular weight is controlled by the addition of chain transfer reagents such as e.g. $\alpha$-(t-butanethiomethyl)styrene etc.

According to WO 2006/086646 A2, the PCS in cross-linked polymers should be able to be reduced by incorporating groups into the polymer network which make a reversible chain cleavage possible. After curing, these groups are activated for example by irradiation with light. This is intended to effect a reversible cleavage of the polymer chains, by which means the PCS is dissipated. To incorporate these groups into the polymer chains, reversible addition-fragmentation chain transfer (RAFT) agents such as e.g. allyl sulphides, dithiocarbamates and thiocarbonates are used.

US 2012/0295228 A1 discloses radically polymerizable dental materials which contain ethylenically unsaturated monomers with disulphide groups which are effective as addition-fragmentation materials and are intended to reduce the PCS.

A disadvantage is that the addition of transfer-active compounds usually leads to a significant reduction in the polymerization rate, above all in the case of reversible systems based on dithioesters. Moreover, in practice, for dental applications the use of mercaptans is ruled out because of their odour and the use of many other RAFT reagents is ruled out because of their colour.

The object of the invention is to provide polymerizable dental materials which, in comparison with the state of the art, are characterized by a delayed gel point and a reduced polymerization shrinkage stress (PCS) with similar mechanical properties. In addition, the materials are to have a more homogeneous network architecture, a narrower and lower glass transition temperature and an improved impact strength. They are furthermore to have an odour which is acceptable for intraoral application and no intrinsic colour.

Figure 1:
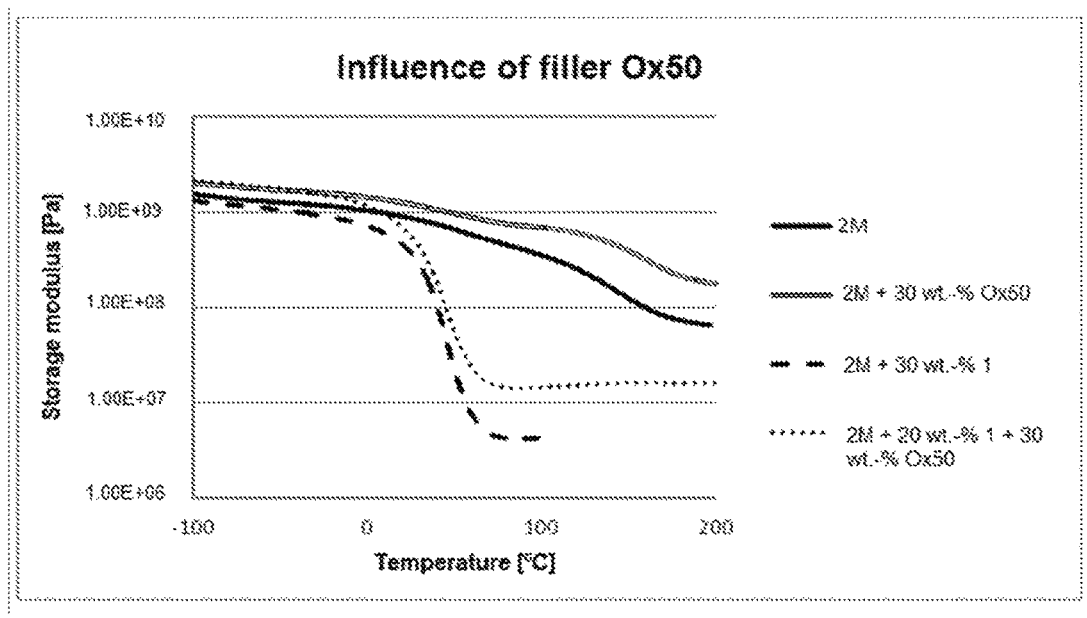
FIG. 1 shows a storage modulus graph for cured resin samples and composites.

The object is achieved according to the invention by a composition which contains a compound of Formula I:

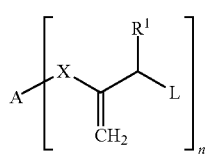

Wherein:

A is H; —CN; a phenyl residue which can carry one or more substituents, such as $CH_3$, $C_2H_5$, OH, $OCH_3$, O—$COCH_3$, a polymerizable vinyl, (meth)acryloyloxy or (meth)acrylamide group; or an aliphatic linear or branched $C_1$-$C_{20}$ alkylene residue which can be interrupted by one or more 1,4-phenylene groups, urethane groups, O or S and which can carry in the terminal position a polymerizable vinyl, (meth)acryloyloxy or (meth)acrylamide group;

$R^1$ is H, an aliphatic linear or branched $C_1$-$C_9$ alkyl residue, tolyl or phenyl;

L is $SR^2$, CO-phenyl, $SO_2R^3$, $PO(R^4R^5)$, $PO(OR^6)(R^7)$, $PO(OR^8)(OR^9)$ or halogen, wherein $R^{2-9}$ in each case independently of each other are a phenyl residue which can carry one or more substituents, such as $CH_3$, $C_2H_5$, OH, $OCH_3$, —O—$COCH_3$, a polymerizable vinyl, (meth)acryloyloxy, (meth)acrylamide group, —C(=$CH_2$)—$COOR^{11}$ or —C(=$CH_2$)—CO—$NR^{12}R^{13}$; or are an aliphatic linear or branched $C_1$-$C_{20}$ alkylene residue which can be interrupted by O or S and which can carry in the terminal position a polymerizable vinyl, (meth)acryloyloxy, (meth)acrylamide group, —C(=$CH_2$)—$COOR^{11}$ or —C(=$CH_2$)—CO—$NR^{12}R^{13}$, wherein $R^{11-13}$ in each case independently of each other are a linear or branched $C_{1-6}$ residue;

X is —COO—, —CON($R^{10}$)— or is absent, wherein the bond to A takes place via O or N and wherein $R^{10}$ is H, or an aliphatic linear or branched $C_1$-$C_{20}$ alkylene residue which can be interrupted by one or more O or S and which can carry in the terminal position a polymerizable vinyl, (meth)acryloyloxy, (meth)acrylamide group, —C(=$CH_2$)—$COOR^{11}$ or —C(=$CH_2$)—CO—$NR^{12}R^{13}$, wherein $R^{11-13}$ in each case independently of each other are a linear or branched $C_{1-6}$ radical;

n is an integer from 1 to 6.

Preferred halogens are chlorine or bromine.

The formula extends only to those compounds which are compatible with the theory of chemical valence. For example, when A is hydrogen, n can only be 1. The indication that a residue is interrupted by one or more aromatics, urethane groups, O, S etc. is to be understood to mean that these groups are inserted into the carbon chain of the residue. These groups are thus bordered on both sides by C atoms and cannot be terminal. $C_1$ residues cannot be interrupted.

The compounds of Formula 1 contain at least one radically polymerizable group, wherein compounds with 2 to 8 and in particular compounds with 2 to 4 radically polymerizable groups are preferred.

The variables preferably have the following meanings:

A H, —CN, a phenyl residue, an aliphatic linear or branched $C_1$-$C_{15}$ alkyl residue which can be interrupted by one or more 1,4-phenylene groups, urethane groups or O and which can carry in the terminal position a polymerizable (meth)acryloyloxy group;

$R^1$ H, phenyl, tolyl, an aliphatic linear $C_1$-$C_3$ alkyl residue;

L $SR^2$ or $SO_2R^3$, wherein $R^{2-3}$ in each case independently of each other an aliphatic linear or branched $C_1$-$C_{20}$ alkylene residue which can be interrupted by O and which can carry in the terminal position a polymerizable (meth)acryloyloxy group or —C(=$CH_2$)—$COOR^{11}$, wherein $R^{11}$ is a linear or branched $C_{1-3}$ residue; or a phenyl residue which can carry one or more substituents, preferably $CH_3$, $C_2H_5$, $OCH_3$ and/or O—$COCH_3$;

X —COO— or —CON($R^{10}$)—, wherein $R^{10}$ is methyl, or is absent;

n 1 or 2.

Particularly preferred are compounds of Formula I in which at least one and preferably all of the variables have the following meaning:

A a saturated, linear aliphatic hydrocarbon residue with 1 to 12 carbon atoms which can be interrupted by one or more 1,4-phenylene groups, urethane groups or O and which can carry a methacryloyloxy group, X —COO— or —CON($R^{10}$)—, wherein $R^{10}$ is methyl, or is absent;

$R^1$ H,

L —$SO_2R^3$, wherein $R^3$ is $CH_3$ or tolyl, n 1 or 2.

Quite particularly preferred are compounds of Formula I in which the variables have the following meanings:

A a saturated, linear aliphatic hydrocarbon residue with 6 to 12 carbon atoms which can be interrupted by 1 to 3 O atoms,

X —COO—;

$R^1$ H,

L $SO_2R^3$, wherein $R^3$ is $CH_3$ or tolyl, n 1 or 2.

Some polymerization-transfer-active compounds of Formula I are known and can be easily prepared using known synthesis methods. Thus the iodine compounds I-L can be added to an unsaturated derivative as shown below and subsequently compounds of Formula I according to the invention are obtained by HI cleavage:

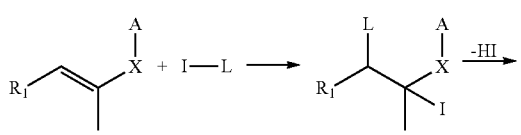

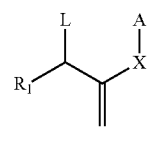

A specific example is:
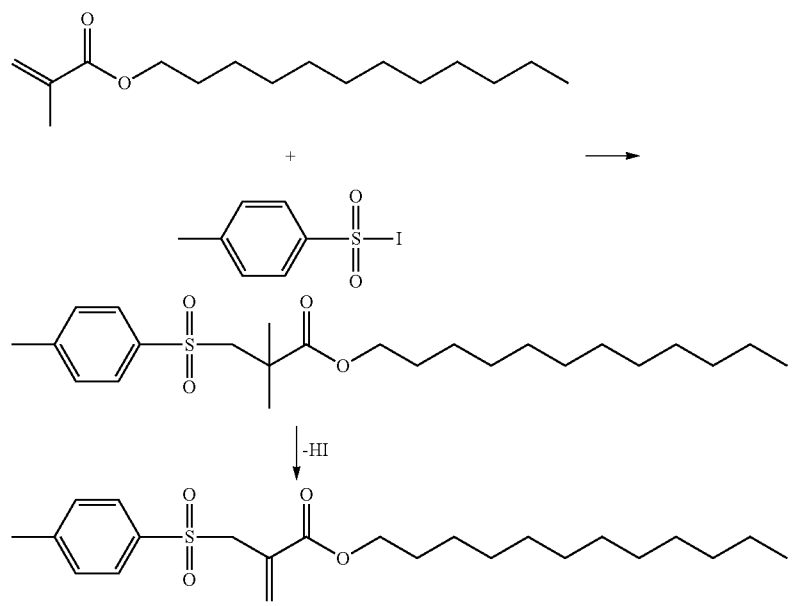
Preferred examples of the polymerization-transfer-active compounds of Formula I according to the invention are:
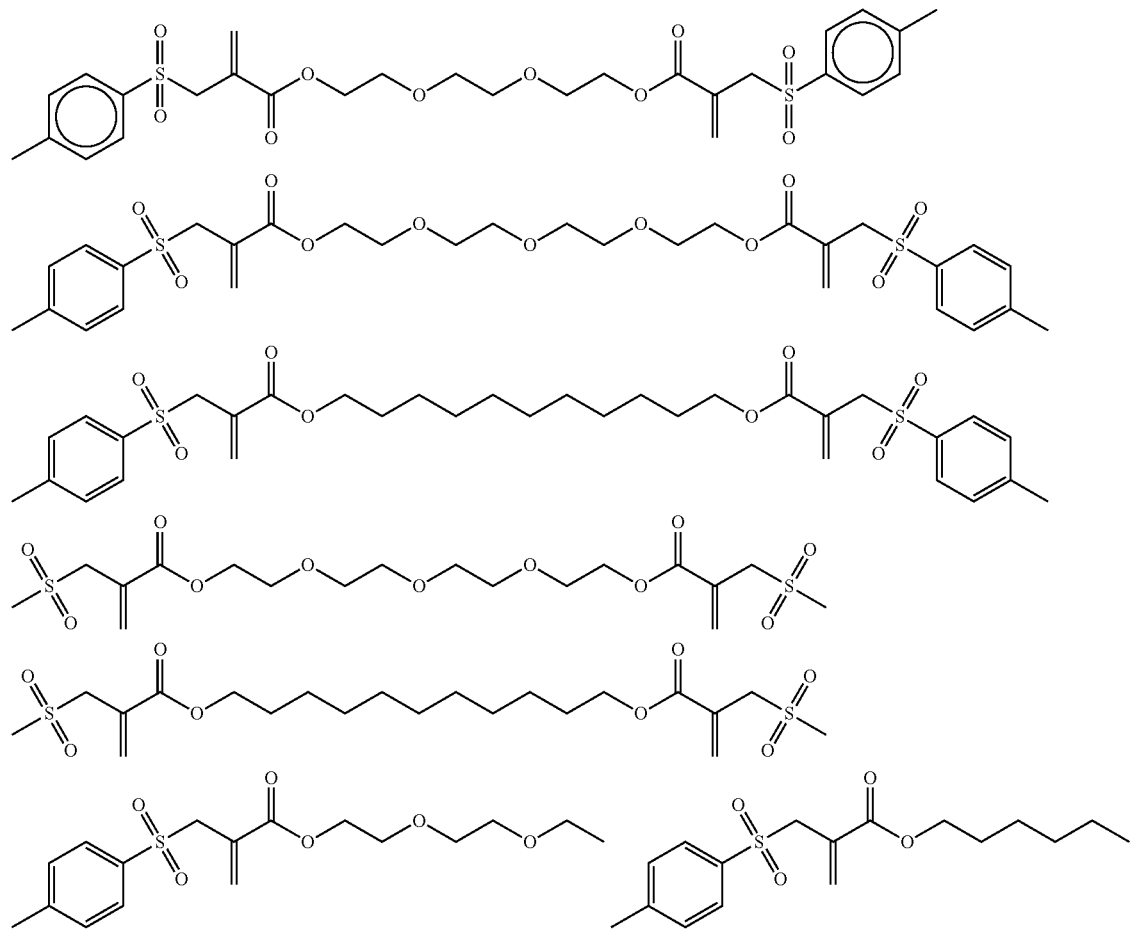

-continued

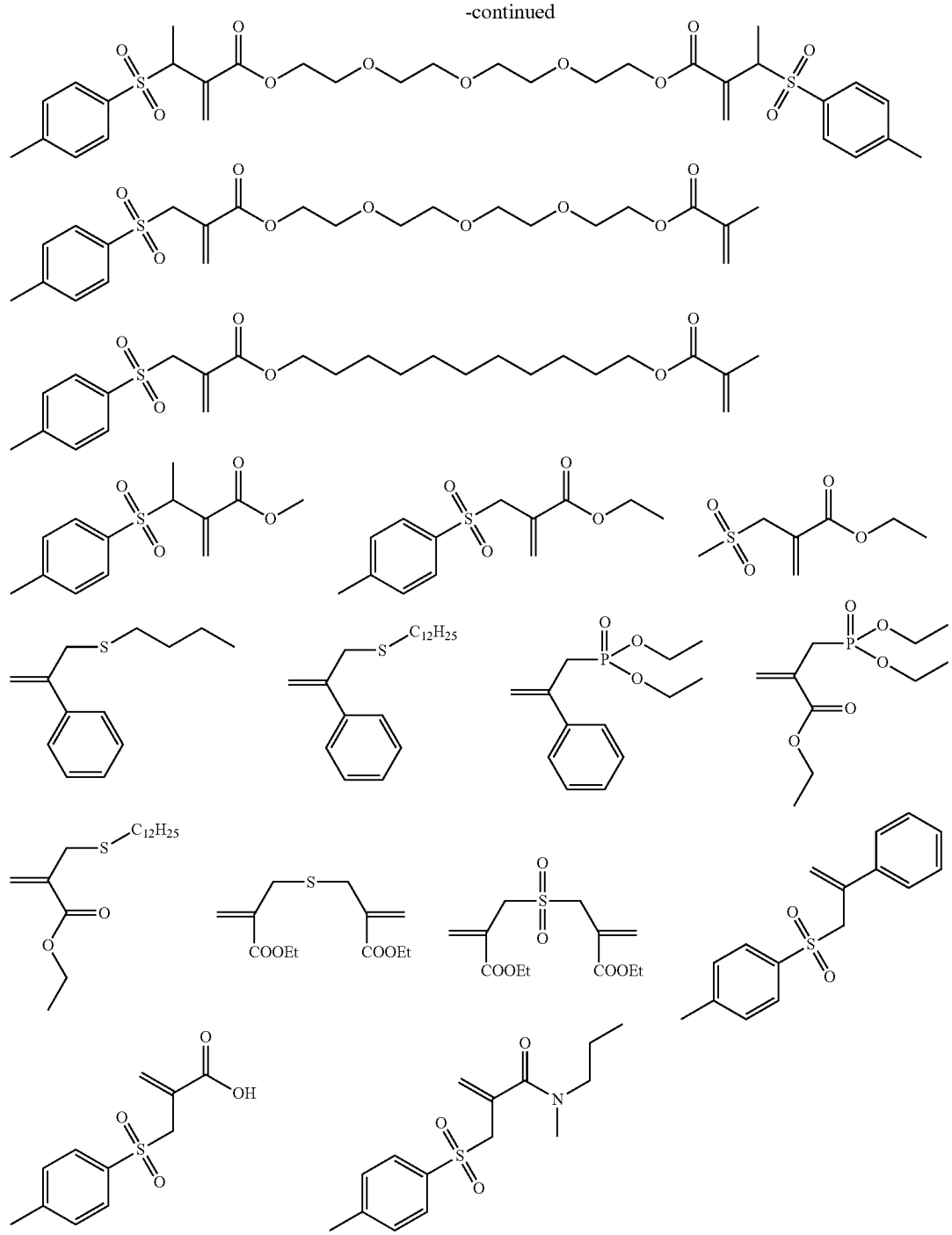

The compounds of Formula I make it possible to control or regulate the network structure during radical polymerization. They lead to a significantly delayed gel formation and thus to a longer gel time, meaning that the 3-dimensional polymer network forms later. A lower PCS is correspondingly achieved during the curing of the resins or corresponding composites, which is a great advantage for a dental application e.g. as filling material. Furthermore, the polymerization-transfer-active compounds of Formula I surprisingly also yield more homogeneous polymer networks with a narrower glass transition, meaning that the glass transition takes place in a narrower temperature range. This has the advantage that chain tensions can be better degraded by relaxation processes and a quicker debonding-on-demand (DoD) can be effected. Moreover, the glass transition temperature is significantly reduced. Finally, the polymerization-transfer-active compounds of Formula I yield polymer materials with improved impact strength, which is mainly attributed to the reduction in the glass transition temperature and the more homogeneous network structure. The reduced glass transition temperature has the further advantage that the polymers can be softened at lower temperatures. This permits, e.g. in the case of adhesives and cements, an on-demand debonding of the adhesive bond (debonding-on-demand).

In addition to the compounds of Formula I, the compositions according to the invention preferably contain at least one radically polymerizable monomer, particularly preferably at least one multifunctional (meth)acrylate or a mixture of mono- and multifunctional (meth)acrylates. By monofunctional (meth)acrylates are meant compounds with one, by polyfunctional (meth)acrylates compounds with two or more, preferably 2 to 4, radically polymerizable groups. According to a quite particularly preferred embodiment, the compositions according to the invention contain at least one dimethacrylate or a mixture of mono- and dimethacrylates.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumyl phenoxyethylene glycol methacrylate (CMP-1E), bisphenol A di(meth)acrylate, bis-G(M)A (an addition product of (meth)acrylic acid and bisphenol-A-diglycidyl ether), ethoxylated or propoxylated bisphenol-A-di(meth)acrylate, such as e.g. the bisphenol-A-dimethacrylate SR-348c (Sartomer) with 3 ethoxy groups or 2,2-bis[4-(2-(meth)acryloxypropoxy)phenyl]-propane, UD(M)A (an addition product of 2-hydroxyethyl (meth)acrylate and 2,2, 4-trimethyl hexamethylene diisocyanate), di-, tri- or tetraethylene glycol di(meth)acrylate, trimethylolpropane tri (meth)acrylate, pentaerythritol tetra(meth)acrylate, as well as glycerol di- and tri(meth)acrylate, 1,4-butanediol di(meth)acrylate, 1,10-decanediol di(meth)acrylate ($D_3MA$) or 1,12-dodecanediol di(meth)acrylate.

Moreover, thermo- or photolabile di(meth)acrylates, such as e.g. the addition product of 2 mol 2-acetoacetoxyethyl methacrylate and 1 mol 2,2,4-trimethylhexamethylene-1,6-diisocyanate (thermolabile) or methacrylic acid-2-[2-(4-{2-methyl-2-[2-(methacryloyloxy)ethylcarbamoyloxy] propionyl}phen-oxy)ethoxycarbonylamino]-ethyl ester are also suitable. These are particularly suitable for the preparation of materials with debonding-on-demand properties.

In addition to the above-named co-monomers, the dental materials according to the invention can preferably also contain radically polymerizable, acid-group-containing monomers (adhesive monomers). Preferred acid groups are carboxylic acid groups, phosphonic acid groups, phosphoric acid groups and sulphonic acid groups. Preferred monomers with carboxylic acid groups are maleic acid, acrylic acid, methacrylic acid, 2-(hydroxymethyl) acrylic acid, 4-(meth)acryloyloxyethyltrimellitic acid anhydride, 10-methacryloyloxydecylmalonic acid, N-(2-hydroxy-3-methacryloyloxypropyl)-N-phenylglycine and 4-vinylbenzoic acid. Preferred monomers with phosphonic acid groups are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentylphosphonic acid, 2-[4-(dihydroxyphosphoryl)-2-oxa-butyl]-acrylic acid, 2-[4-(dihydroxyphosphoryl)-2-oxa-butyl]-acrylic acid ethyl and -2,4,6-trimethylphenyl esters. Preferred monomers with phosphoric acid groups are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritolpentamethacryloyloxyphosphate, 10-methacryloyloxydecyl dihydrogen phosphate, phosphoric acid mono-(1-acryloyl-piperidin-4-yl)ester, 6-(methacrylamidohexyl) dihydrogen phosphate and 1,3-bis-(N-acryloyl-N-propylamino)-propan-2-yl dihydrogen phosphate. Preferred monomers with sulphonic acid groups are vinylsulphonic acid, 4-vinylphenylsulphonic acid and 3-(methacrylamido) propyl sulphonic acid.

To initiate the radical polymerization, the compositions according to the invention preferably contain an initiator for the radical polymerization, particularly preferably a photoinitiator. Suitable in particular as photoinitiators are benzophenone, benzoin and derivatives thereof or α-diketones or derivatives thereof, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are preferably used, and particularly preferably α-diketones combined with amines as reducing agents, such as e.g. 4-(dimethylamino)-benzoic acid ester (EDMAB), N,N-dimethylaminoethyl methacrylate, N,N-dimethyl-sym.-xylidine or triethanolamine. Norrish type I photoinitiators, above all acyl or bisacylphosphine oxides are also suitable, and monoacyltrialkyl or diacyldialkyl germanium compounds, such as e.g. benzoyltrimethylgermanium, dibenzoyldiethylgermanium or bis(4-methoxybenzoyl)diethylgermanium (MBDEGe) are particularly suitable. Mixtures of the different photoinitiators can also be used, such as e.g. bis(4-methoxybenzoyl)diethylgermanium combined with camphorquinone and 4-dimethylaminobenzoic acid ethyl ester.

According to a preferred embodiment, the dental materials according to the invention additionally contain organic or preferably inorganic particulate filler, particularly preferably one or more inorganic particulate fillers.

Particularly suitable are fillers based on oxides with a particle size of from 0.01 to 15 μm, such as $SiO_2$, $ZrO_2$ and $TiO_2$ or mixed oxides of $SiO_2$, $ZrO_2$, ZnO and/or $TiO_2$, nanoparticulate or microfine fillers with a particle size of from 10 to 300 nm, such as pyrogenic silica or precipitated silica as well as glass powders with a particle size of from 0.01 to 15 μm, preferably from 0.2 to 1.5 μm, such as quartz, glass ceramic or X-ray opaque glass powders of e.g. barium or strontium aluminium silicate glasses, and X-ray opaque fillers with a particle size of from 0.2 to 5 μm, such as ytterbium trifluoride, tantalum(V) oxide, barium sulphate or mixed oxides of $SiO_2$ with ytterbium(III) oxide or tantalum (V) oxide. Fibrous fillers, nanofibres or whiskers are also not excluded. Unless otherwise indicated, all particle sizes are weight-average particle sizes.

The fillers are divided, according to particle size, into macrofillers and microfillers. Macrofillers are obtained by grinding quartz, X-ray opaque glasses, borosilicates or ceramic, are of a purely inorganic nature and mostly consist of splinter-like parts. Macrofillers with an average particle size of from 0.2 to 10 μm are preferred. Pyrogenic $SiO_2$ or precipitated silica are preferably used as microfillers, or also mixed oxides, e.g. $SiO_2$—$ZrO_2$, which are available by hydrolytic co-condensation of metal alkoxides. The microfillers preferably have an average particle size of from approx. 5 to 100 nm.

To improve the bond between the filler particles and the cross-linked polymerization matrix, $SiO_2$-based fillers can be surface-modified with (meth)acrylate-functionalized silanes. An example of such silanes is 3-(meth)acryloyloxypropyltrimethoxysilane. To surface-modify non-silicate fillers, such as e.g. $ZrO_2$ or $TiO_2$, functionalized acid phosphates, such as e.g. 10-(meth)acryloyloxydecyl dihydrogen phosphate can also be used.

The fill level is geared to the desired intended use. Filling composites preferably have a filler content of 75-90 wt.-% and composite cements a filler content of 50-75 wt.-%.

Preferred dental materials thus contain, in addition to at least one compound of Formula (I), additionally at least one radically polymerizable monomer, in particular at least one multifunctional (meth)acrylate or a mixtures of mono- and multifunctional (meth)acrylates, at least one initiator for the radical polymerization and preferably also at least one filler.

Optionally, the compositions used according to the invention can contain further additives, above all stabilizers, dyes, microbiocidal active ingredients, fluoride-ion-releasing additives, gas-releasing additives, optical brighteners, plasticizers or UV absorbers.

The dental materials according to the invention preferably contain 0.5 to 60 wt.-%, preferably 1.0 to 50 wt.-% and particularly preferably 1.0 to 40 wt.-% of at least one compound of general formula I.

In addition, the materials preferably also contain 0.01 to 5.0 wt.-%, preferably 0.1 to 5.0 wt.-% and particularly preferably 0.1 to 3.0 wt.-% initiator(s) for the radical polymerization, particularly preferably a photoinitiator, and particularly preferably also 5 to 80 wt.-%, preferably 10 to 70 wt.-% and particularly preferably 10 to 60 wt.-% multifunctional (meth)acrylate(s).

Furthermore, the dental materials according to the invention preferably contain 0 to 90 wt.-%, preferably 5 to 90 wt.-% and particularly preferably 5 to 80 wt.-% filler(s), wherein the filler content is matched to the planned use of the materials, as described above.

Moreover, the dental materials according to the invention preferably contain 0 to 5 wt.-%, preferably 0 to 3 wt.-%, particularly preferably 0.2 to 3 wt.-% other additive(s).

According to the invention, dental materials which contain the following components are particularly preferred:
(a) 5 to 80 wt.-%, preferably 10 to 70 wt.-% and particularly preferably 10 to 60 wt.-% multifunctional (meth)acrylate(s),
(b) 0.01 to 5.0 wt.-%, preferably 0.1 to 5.0 wt.-% and particularly preferably 0.1 to 3.0 wt.-% initiator(s),
(c) 0.5 to 60 wt.-%, preferably 1.0 to 50 wt.-% and particularly preferably 1.0 to 40 wt.-% of at least one compound of general formula I,
(d) 0 to 50 wt.-%, preferably 0 to 40 wt.-% and particularly preferably 0 to 30 wt.-% monofunctional (meth)acrylate(s),
(e) 0 to 90 wt.-%, preferably 5 to 90 wt.-% and particularly preferably 5 to 80 wt.-% filler(s), and
(f) 0 to 5 wt.-%, preferably 0 to 3 wt.-% and particularly preferably 0.2 to 3 wt.-% additive(s).

Unless otherwise stated, all quantities relate to the total mass of the materials. The above individual quantity ranges can be chosen separately.

Those dental materials that consist of the named components are particularly preferred. Furthermore, those materials are preferred in which the individual components are in each case selected from the above-named preferred and particularly preferred substances. Particularly preferred are moreover materials which, in addition to the compound of Formula (I), do not contain volatile mercaptans, i.e. mercaptans which have a typical mercaptan odour. Quite particularly preferred are compositions which do not contain further mercaptans and preferably also do not contain other sulphur compounds.

The dental materials according to the invention are particularly suitable as dental cements, filling composites and veneering materials, and as materials for manufacturing inlays, onlays, crowns and bridges. They have similar mechanical properties (bending strength and elastic modulus) to materials based on dimethacrylates, but are characterized by a reduced polymerization shrinkage stress (PCS), improved impact strength and low intrinsic odour.

The dental materials are suitable primarily for intraoral application by the dentist to restore damaged teeth (clinical materials), e.g. as dental cements, filling composites and veneering materials. However, they can also be used extraorally, for example in the manufacture or repair of dental restorations, such as inlays, onlays, crowns and bridges (technical materials).

The invention is explained in more detail below by means of examples.

EXAMPLES

Example 1

Synthesis of 2-(toluene-4-sulfonylmethyl)-acrylic acid lauryl ester (1)

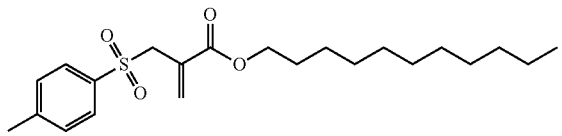 [SMILES: C=C(CS(=O)(=O)c1ccc(C)cc1)C(=O)OCCCCCCCCCCC]

First of all, in a yellow-light laboratory, 3.81 g (15 mmol) iodine was dissolved in 70 ml ethanol and slowly added dropwise to a 0.1 M solution of sodium p-toluene sulfinate (15 mmol) in water. The yellow solid that forms (4-methylbenzene-1-sulfonyl iodide, MBSI) was filtered and subsequently washed with water. The solid was then dissolved in $CH_2Cl_2$ (50 ml) and dried with anhydrous $Na_2SO_4$. The desiccant was filtered and the solution with the freshly prepared MBSI was stirred together with 2.54 g (10 mmol) lauryl methacrylate (LMA). The reaction was monitored using thin-layer chromatography (PE/EE 20/1). After all of the LMA had been used up, the reaction solution was washed with 5 wt.-% sodium dithionite solution (2×25 ml) and with water (1×25 ml). The aqueous phase was re-extracted with $CH_2Cl_2$ (1×25 ml) and the combined organic phases were dried over anhydrous $Na_2SO_4$. 50 ml ethyl acetate was then added to the solution and the $CH_2Cl_2$ was evaporated on a rotary evaporator. 5.06 g (50 mmol) triethylamine was then added to the reaction solution under an Ar atmosphere and then boiled under reflux overnight. Once the reaction was complete, the solution was washed with 1N HCl (2×50 ml) and dist. water (1×50 ml). The aqueous phases were re-extracted and the combined organic phases were dried over anhydrous $Na_2SO_4$. The solvent was drawn off on a rotary evaporator and the crude product was purified using column chromatography with a mixture of PE/EE 5/1 ($R_f$=0.39). The yield was approx. 28.8 g (73% theoretical).

$^1$H-NMR (200 MHz, $CDCl_3$, δ): 7.71 (d, J=8.2 Hz, 2H; Ar—H), 7.30 (d, J=8.2 Hz, 2H; Ar—H), 6.47 (s, 1H; =$CH_2$), 5.89 (s, 1H; =$CH_2$), 4.12 (s, 2H; —$SO_2$—$CH_2$—), 3.94 (t, 2H; —O—$CH_2$—$CH_2$—), 2.42 (s, 3H; Ar—$CH_3$), 1.52 (m, 2H; —O—$CH_2$—$CH_2$—), 1.25 (s, 18H; —O—$CH_2$—$CH_2$—$CH_2$—$CH_2$—$CH_2$—$CH_2$—$CH_2$—$CH_2$—$CH_2$—$CH_2$—$CH_3$); 0.86 (m, 3H; —$CH_2$—$CH_3$);

$^{13}$C-NMR (50 MHz, $CDCl_3$, δ): 164.9 (C=O), 144.8 ($C_4$), 135.5 ($C_4$), 133.1 ($C_2$), 129.6 ($C_3$), 129.2 ($C_4$), 128.8

($C_3$), 65.6 ($C_2$), 57.5 ($C_2$), 31.9 ($C_2$), 29.6 ($C_2$, $C_2$, $C_2$), 29.5 ($C_2$), 29.3 ($C_2$), 29.2 ($C_2$), 28.4 ($C_2$), 25.8 ($C_2$), 22.7 ($C_2$), 21.6 ($C_1$), 14.1 ($C_1$).

Example 2

Synthesis of tetraethylene glycol bis[2-(toluene-4-sulfonylmethyl) acrylate] (2)

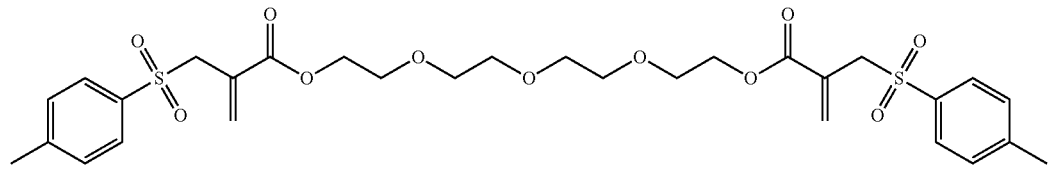

Tetraethylene glycol dimethacrylate (TTEGDMA: 5.29 g, 16 mmol) and 4-toluenesulfonyl iodide (9.03 g, 32 mmol) were stirred together in $CH_2Cl_2$ (approx. 50 ml) at room temperature in yellow light. The reaction was monitored using $^1$H-NMR spectroscopy. After all of the TTEGDMA had been used up (decrease in the double-bond signals), the reaction solution was washed with 5 wt.-% sodium dithionite solution (2×25 ml) and with water (1×25 ml). The aqueous phase was re-extracted with $CH_2Cl_2$ (1×25 ml) and the combined organic phases were dried over $Na_2SO_4$. 50 ml ethyl acetate was then added to the solution and the $CH_2Cl_2$ was evaporated on a rotary evaporator. A further 50 ml ethyl acetate was then added to the reaction solution and triethylamine (8.1 g, 80 mmol) was added dropwise under an Ar atmosphere (solid precipitated out). The reaction solution was then boiled under reflux overnight. Once the reaction was complete, the solution was washed with 1N HCl (2×50 ml) and dist. water (1×50 ml). The aqueous phases were re-extracted and the combined organic phases were dried over $Na_2SO_4$. The solvent was drawn off on a rotary evaporator and the crude product was purified using column chromatography with a mixture of PE/EE 1/4. ($R_f$~0.32). Yield 70%.

$^1$H-NMR (200 MHz, $CDCl_3$, δ): 7.73 (d, J=8.2 Hz, 4H; Ar—H), 7.32 (d, J=8.2 Hz, 4H; Ar—H), 6.52 (s, 2H; =$CH_2$), 5.89 (s, 2H; =$CH_2$), 4.14 (m, 8H; OOC—$CH_2$—, $SO_2$—$CH_2$—), 3.62 (m, 12H; —$CH_2$—O—$CH_2$—$CH_2$—), 2.43 (s, 6H; Ar—$CH_3$).

$^{13}$C-NMR (50 MHz, $CDCl_3$, δ): 164.9 (C=O), 144.9 ($C_4$), 135.4 ($C_4$), 133.6 ($C_2$), 129.7 ($C_3$), 128.9 ($C_4$), 128.8 ($C_4$), 70.7 ($C_2$), 68.8 ($C_2$), 64.5 ($C_2$), 57.5 ($C_2$), 21.6 ($C_1$).

Example 3

Synthesis of triethylene glycol bis[2-(toluene-4-sulfonylmethyl) acrylate] (3)

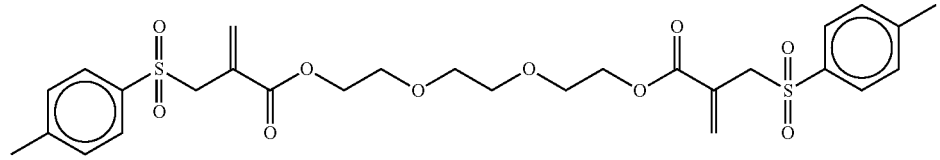

In a brown glass flask, sodium p-toluenesulfinate (39.20 g, 0.22 mol) was reacted with iodine (55.83 g, 0.22 mol) and worked up according to Example 1 to prepare MBSI 1. The yellow solid was dissolved in dichloromethane (300 ml). Triethylene glycol dimethacrylate (28.63 g, 0.10 mol) was added and the reaction mixture was stirred at RT. After 24 h triethylamine (22.26 g, 0.22 mol) was added dropwise. The red-brown solution was stirred for 2 h at ambient temperature and then concentrated on a rotary evaporator. The dark brown oil was taken up in n-hexane/ethyl acetate 1:1 (100 ml) and filtered over a frit filled with silica gel (silica gel 60, n-hexane/ethyl acetate 1:1). The filtrate was concentrated on a rotary evaporator. The residue was dissolved in ethyl acetate (400 ml) and triethylamine (22.26 g, 0.22 mol) was added. The brownish solution was heated under reflux for 6 h. After cooling, the reaction solution was washed with hydrochloric acid (1N; 2×200 ml) and water (200 ml), dried over $Na_2SO_4$, filtered and concentrated on a rotary evaporator. The brownish oil was purified using column chromatography (silica gel 60, n-hexane/ethyl acetate 1:2; $R_f$=0.35). 48.44 g (81% yield) of a yellow oil was obtained.

$^1$H-NMR (200 MHz, $CDCl_3$, δ): 7.73 (d, J=8.2 Hz, 4H; Ar—H), 7.32 (d, J=8.2 Hz, 4H; Ar—H), 6.52 (s, 2H; =$CH_2$), 5.89 (s, 2H; =$CH_2$), 4.14 (m, 8H; OOC—$CH_2$—, $SO_2$—$CH_2$—), 3.62 (m, 12H; —$CH_2$—O—$CH_2$—$CH_2$—), 2.43 (s, 6H; Ar—$CH_3$);

$^{13}$C-NMR (50 MHz, $CDCl_3$, δ): 164.9 (C=O), 144.9 ($C_4$), 135.4 ($C_4$), 133.6 ($C_2$), 129.7 ($C_3$), 128.9 ($C_4$), 128.8 ($C_4$), 70.7 ($C_2$), 68.8 ($C_2$), 64.5 ($C_2$), 57.5 ($C_2$), 21.6 ($C_1$);

Example 4

Preparation of Composites with Transfer Reagent 1 from Example 1

A 1/1 mixture (mol/mol) of the monomers UDMA and $D_3$MA was prepared (resin mixture 2M). Part of this mixture was mixed with monomer 1 from Example 1. The second mixture had the following composition: UDMA (39 wt.-%), $D_3$MA (26 wt.-%) and 1 (35 wt.-%). The photoinitiator Ivocerin® (1 wt.-%) was added to both mixtures. Composite pastes based on these mixtures were prepared by adding 30 wt.-% of the pyrogenic silicic acid Ox50. The composite paste with monomer 1 had the total composition: UDMA (27 wt.-%), $D_3$MA (18 wt.-%), 1 (24.3 wt.-%), initiator (0.7 wt.-%) and Ox50 (30 wt.-%). The formulations were poured into silicone moulds and polymerized in a Lumamat 100

(Ivoclar AG) using program 2 (P2: 10 min irradiation with an intensity of approx. 20 mW/cm$^2$). The rods were turned and cured again using P2. The test rods were ground and then measured on an Anton Paar Rheometer MCR301 with a CTD oven (Convection Temperature Control) and an installed solid-clamping device (SRF12 for rectangular cross-sections up to 12 mm). The heating rate set was 2° C./min. All samples were heated from −100° C. to 200° C. and oscillated at a constant frequency of 1 Hz and 0.1% deflection. The storage modulus graphs represented in FIG. 1 show that the addition of transfer reagent 1 both in the case of the cured resin sample and in the case of the composite similarly leads to a reduction in the glass transition temperature and to a deeper and significantly narrower glass transition range.

| Formulation | $T_G$ [° C.] |
| --- | --- |
| 2M$^{a)}$* | 148 |
| 2M + Ox50* | 162 |
| 2M + monomer 1 | 50 |
| 2M + monomer 1 + Ox50 | 50 |

$^{a)}$2M: UDMA/D$_3$MA (1/1)
*Comparison example

Example 5

Preparation of Composites with Transfer Reagent 2 from Example 2

Figure 2:
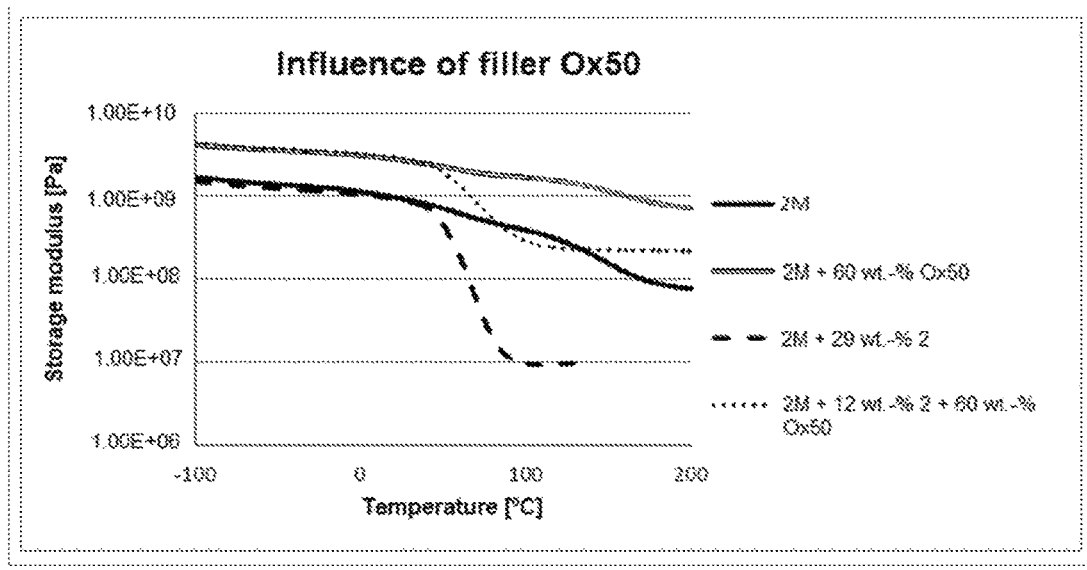
FIG. 2 shows a storage modulus graph for cured resin samples and composites of different compositions than shown in FIG. 1.

Test pieces were prepared and investigated analogously to Example 4. The following formulations were used: 1/1 mixture (mol/mol) of UDMA and D$_3$MA (mixture 2M) and a mixture of UDMA (43 wt.-%), D$_3$MA (28 wt.-%) with monomer 2 (29 wt.-%). Corresponding composite pastes were obtained by adding 60 wt.-% Ox50. The composite paste with monomer 2 had the following total composition: UDMA (17 wt.-%), D$_3$MA (11 wt.-%), 2 (12 wt.-%) and Ox50 (60 wt.-%). FIG. 2 again shows the storage modulus as a function of the temperature for the unfilled and filled resins. The storage modulus graphs shown in FIG. 2 show that the addition of transfer reagent 2 (Example 2) both in the case of the unfilled resin and in the case of the composite leads to a significantly narrower glass transition range with a reduced glass transition temperature ($T_G$)

| Formulation | $T_g$ [° C.] |
| --- | --- |
| 2M$^{a)}$* | 148 |
| 2M + Ox50* | 157 |
| 2M + monomer 2 | 73 |
| 2M + monomer 2 + Ox50 | 78 |

$^{a)}$2M: UDMA/D$_3$MA (1/1)
*Comparison example

Example 6

Preparation of Filling Composites with Transfer Reagent 3 from Example 3

The composites were prepared in a Linden kneader. For this, two monomer mixtures were prepared first of all: Monomer mixture A (all values in mass-%): Bis-GMA (28.9%), UDMA (26.0%), SR-348c (14.1%), chain transfer reagent 3 (30.0%), photoinitiator (CQ, 0.2%), EDMAB (0.4%), MBDEGe (0.05%), Lucerin TPO (2,4,6-trimethyl-benzoyl diphenylphosphine oxide; 0.25%), stabilizer (hydroquinone monomethyl ether (MEHQ), 0.1%). Monomer mixture B: Bis-GMA (41.3%), UDMA (37.4%), SR-348c (20.3%), CQ (0.2%), EDMAB (0.4%), MBDEGe (0.05%), Lucerin TPO (0.25%), MEHQ (0.1%). To prepare composites, 22.5 mass-% of monomer mixture A (composite A) or monomer mixture B (composite B) was incorporated in each case with 77.5 mass-% of a filler mixture (17% Tetric EvoCeram isofiller (Ivoclar Vivadent AG), 45.5% silanized Ba—Al-borosilicate glass filler (average particle size of 0.7 µm, Schott), 10% Spherosil (silanized SiO$_2$—ZrO$_2$ mixed oxide, average particle size of 1.2 µm, Tokoyama Soda), 5% YbF$_3$ (ytterbium trifluoride, average particle size of 0.2 µm, Auer-Remy; the percentages relate in each case to the total mass of the composite). From the materials, bending test rods with a length of 20 mm and a cross-section of 2×2 mm were prepared which were irradiated twice for 3 minutes with a dental light source (Spectramat®, Ivoclar Vivadent AG) and thus cured. The bending strength and the bending E modulus were determined according to ISO standard 4049 (Dentistry—Polymer-based filling, restorative and luting materials). To determine the polymerization shrinkage force (PF), the samples were fixed on one side to a silanized object holder and bonded to a Zwick universal testing machine using a steel post (d=10 mm) treated with the Monobond adhesion promoter (Ivoclar Vivadent AG). After setting the layer thickness (0.8 mm) and removing the excess, the measurement was started.

The illumination (Bluephase 20i, high power, 10 s) was carried out through the object holder and started 120 s after the start of the measurement. The change in force while keeping the crosshead position constant was recorded over a total of 10 minutes. The PCS was obtained by dividing the measured force by the surface area of the test pieces. The resulting measured values are collated in Table 1. The results demonstrate that composite sample A with a compound of Formula I exhibits a significantly reduced polymerization shrinkage force and at the same time does not have worse mechanical properties compared with reference composite B.

TABLE 1

Properties of the composites

| Property | Composite A | Composite B* |
| --- | --- | --- |
| Bending strength (MPa) after 24 h | 105.3 ± 5.9 | 115.0 ± 12.9 |
| Bending strength (MPa) after 24 h WS$^{1)}$ | 140.9 ± 10.3 | 129.1 ± 8.0 |
| Bending E modulus (GPa) after 24 h | 9.57 ± 0.73 | 10.23 ± 0.38 |
| Bending E modulus (GPa) after 24 h WS | 9.91 ± 0.56 | 10.00 ± 0.20 |
| PCS (MPa) after 80 s | 0.18 | 0.26 |
| PCS (MPa) after 480 s | 0.23 | 0.30 |

$^{1)}$WS = water storage of the test pieces
*Comparison example

Example 7

Measurement of the Impact Strength (Dynstat Impact Test)

The impact strength properties were determined using the DYNSTAT apparatus in accordance with DIN 53435, wherein the impact strength (impact energy) of unnotched test pieces was determined in the impact bending apparatus. Sample rods (~1×0.45×0.15 cm) were prepared from the formulations named in Table 2 and Dynstat impact tests were carried out using a 2-kg/cm hammer (0.2 J). The values obtained are listed in Table 2 given below.

TABLE 2

| Impact strength | |
|---|---|
| Formulation | Impact energy [kJ/m$^2$][a] |
| 2M[b]* | 4.0 |
| 2M + monomer 2 (25 wt.-%) | 6.8 |
| 2M + monomer 2 (29 wt.-%) | 18.0 |

[a]Standardized for width and thickness
[b]2M: UDMA/D$_3$MA (1/1)
*Comparison example It can be clearly seen that an increase in impact strength was achieved. The impact strength was increased by more than 50% in the case of a proportion of 25 wt.-% of compound 2 (transfer reagent).

Example 8

Synthesis of 2-propenoic acid 2-[(diethoxyphosphinyl)-methyl]-ethyl ester (4)

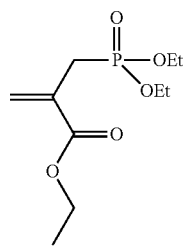 [SMILES: C=C(CP(=O)(OCC)OCC)C(=O)OCC]

For the synthesis of 4, ethyl 2-bromomethylacrylate (1.5 g, 0.008 mol) was heated under reflux with distilled triethyl phosphite (1.3 g, 0.008 mol) for 7 h under an Ar atmosphere in a 10-ml round-bottomed flask and then reacted for 12 h at RT. The product was transferred into a pear-shaped flask and EtBr (bp=38° C. at 1.013 bar) was removed at 5 mbar. Purification using MPLC with petroleum ether (PE)/ethyl acetate (EE) 3:2 was then carried out (Rf~0.13). The yield of 4 purified using column chromatography was 1.6 g (82% theoretical).

$^1$H-NMR (200 MHz, CDCl$_3$, δ): 0.92-1.34 (9.1H, m, 3× —CH$_2$—CH$_3$), 2.77 (1H, d, J=0.78 Hz, =C(COOEt)-CH$_2$—PO(OEt)$_2$), 2.87 (1H, d, J=0.78 Hz, =C(COOEt)-CH$_2$—PO(OEt)$_2$), 3.87-4.18 (6.1H, m, 3× —O—CH$_2$—CH$_3$), 5.73 (1H, dd, J=5.46 Hz, J=0.78 Hz, H$_2$C=C(COOEt)-), 6.22 (1H, dd, J=5.66 Hz, J=0.58 Hz, H$_2$C=C(COOEt)-).

Example 9

Synthesis of 2-propenoic acid 2-[(dodecylthio)methyl]-ethyl ester (5)

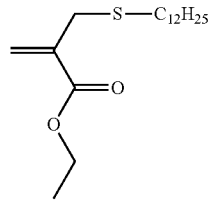

For the synthesis of 5, triethylamine (1.1 g, 0.011 mol) and freshly distilled dodecylthiol (1.6 g, 0.008 mol) were placed in a 50-ml round-necked flask with 10 ml THF and ethyl 2-bromomethylacrylate (1.5 g, 0.008 mol) were flushed into the reaction flask with 9 ml THF. On addition of the acrylate a fine, white precipitate precipitated out immediately. The end of the reaction, after stirring at room temperature (RT) for 21 h, was confirmed using thin-layer chromatography (TLC). The working up was carried out by dissolving unreacted salt in 15 ml deionized water. The aqueous phase was extracted 3× with 15 ml petroleum ether, the combined organic phases were dried over Na$_2$SO$_4$ and PE was drawn off on a rotary evaporator. Purification using medium-pressure liquid chromatography (MPLC) with PE/EE 10:1 was then carried out (R$_f$~0.46 (PE/EE 12:1)). The yield of 5 purified using column chromatography was 1.2 g (50% theoretical).

$^1$H-NMR (200 MHz, CDCl$_3$, δ): 0.85 (3.5H, t, J=6.46 Hz, —C$_{10}$H$_{20}$—CH$_3$), 1.10-1.65 (27.1H, m, —CH$_2$—C$_{10}$H$_{20}$—CH$_3$ and —O—CH$_2$—CH$_3$), 2.42 (2.1H, t, J=7.24 Hz, —S—CH$_2$—C$_{11}$H$_{23}$), 3.35 (2H, s, =C(COOC$_2$H$_5$)—CH$_2$—S—), 4.21 (2.2H, q, J=7.11 Hz, —O—CH$_2$—CH$_3$), 5.61 (1H, d, J=1.17 Hz, H$_2$C=C(COOC$_2$H$_5$)—), 6.17 (1H, d, J=1.98 Hz, H$_2$C=C(COOC$_2$H$_5$)—).

Example 10

Synthesis of 2-{[2-(ethoxycarbonyl)-2-propenyl]-sulfanyl]-methyl}-acrylic acid ethyl ester (6)

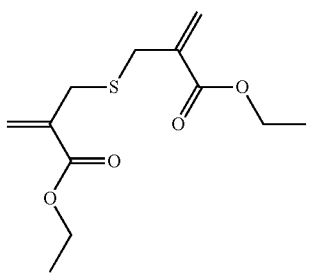 [SMILES: C=C(CSCC(=C)C(=O)OCC)C(=O)OCC]

For the synthesis of 6, ethyl 2-bromomethylacrylate (10.0 g, 0.052 mol) was placed in a 50-ml round-bottomed flask and sodium sulfide (5.9 g, 0.021 mol), freshly recrystallized from deionized H$_2$O, in 2 ml deionized H$_2$O was added in one go and rinsed using 8 ml H$_2$O. Stirring was carried out for 24 h at RT and, after controlling the reaction using TLC, dilution was carried out with 15 ml deionized H$_2$O to dissolve any salt formed. Extraction was carried out 3× with 15 ml petroleum ether, the combined organic phases were extracted with saturated saline solution and then dried over Na$_2$SO$_4$. After drawing off the solvent on a rotary evaporator, purification was carried out using MPLC in PE/EE 6:1 (R$_f$~0.49) and yielded 4.0 g 6 (30% theoretical yield).

$^1$H-NMR (200 MHz, CDCl$_3$, δ): 1.18 (6.1H, t, J=7.13 Hz, 2× —CH$_2$—CH$_3$), 3.20 (3.8H, d, J=0.58 Hz, 2× =C(COOC$_2$H$_5$)—CH$_2$—S—), 4.10 (4.1H, q, J=7.11 Hz, —O—CH$_2$—CH$_3$), 5.55 (2H, d, J=0.98 Hz, 2× H$_2$C=C(COOC$_2$H$_5$)—), 6.09 (2H, d, J=0.98 Hz, 2× H$_2$C=C(COOC$_2$H$_5$)—).

Example 11

Synthesis of 2-{[2-(ethoxycarbonyl)-2-propenyl]-sulfonyl]-methyl}-acrylic acid ethyl ester (7)

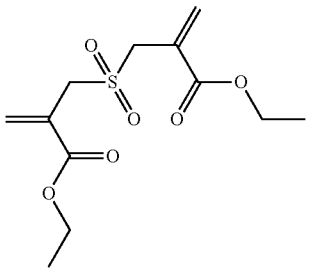 [SMILES: C=C(CS(=O)(=O)CC(=C)C(=O)OCC)C(=O)OCC]

For the synthesis of 7, compound 6 (3.0 g, 0.012 mol) in 100 ml DMF was placed in a 500-ml round-necked flask, potassium peroxosulfate (13.9 g, 0.045 mol) was added and rinsed with 200 ml DMF. Stirring was carried out for 4 h at RT under an Ar atmosphere and, after controlling the reaction using TLC, deionized H$_2$O (900 ml) was added. Extraction was carried out 3× with 130 ml diethyl ether, 1× with 150 ml saturated saline solution, followed by drying over Na$_2$SO$_4$. After drawing off the solvent on a rotary evaporator, purification was carried out using MPLC in PE/EE 10:1 (R$_f$~0.67 (PE/EE 1:1)) and yielded 1.2 g 7 (37% theoretical yield).

$^1$H-NMR (200 MHz, CDCl$_3$, δ): 1.24 (6.4H, t, J=7.14 Hz, 2× —CH$_2$—CH$_3$), 4.03 (4.1H, s, 2× =C(COOC$_2$H$_5$)—CH$_2$—S—), 4.18 (4.1H, q, J=7.17 Hz, —O—CH$_2$—CH$_3$), 6.08 (2H, s, 2× H$_2$C=C(COOC$_2$H$_5$)—), 6.53 (2H, s, 2× H$_2$C=C(COOC$_2$H$_5$)—).

Example 12

Synthesis of 2-(tosylmethyl)acrylonitrile (8)

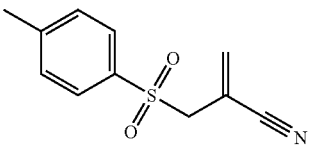

Tosyl iodide (4.88 g, 17 mmol) and methacrylonitrile (1.16 g, 17 mmol) were dissolved in 100 ml carbon tetrachloride and stirred at room temperature for 4 h. The solvent and any iodine formed were then evaporated under vacuum. After the renewed addition of 100 ml carbon tetrachloride, the solution had 4 equivalents of triethylamine added to it and was heated under reflux for 12 h. The resulting brown solution was washed with 5% sodium dithionite solution (2×20 ml), 1N HCl (1×20 ml) and saturated NaCl solution (1×20 ml) to remove any remaining iodine and triethylamine. The collected organic phases were dried over 15 g Na$_2$SO$_4$ and the solvent drawn off on a rotary evaporator. The crude product was purified using column chromatography with pure dichloromethane as mobile solvent. The yield was 789 mg (21% theoretical) 2-(tosylmethyl)acrylonitrile 8 as fine white needles.

$^1$H-NMR (200 MHz, CDCl$_3$) δ=7.73 (d, 8.45 Hz, 2H; Ar—H), 7.33 (d, J=8.45 Hz, 2H; Ar—H), 6.15 (s, 1H; C=H$_2$), 5.94 (s, 1H; C=H$_2$), 3.84 (s, 2H; —SO$_2$—CH$_2$—), 2.41 (s, 3H; Ar—CH$_3$) ppm.

Example 13

Synthesis of 1-methyl-4-((2-phenylallyl)sulfonyl)benzene (9)

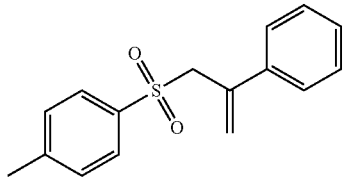 [SMILES: C=C(CS(=O)(=O)c1ccc(C)cc1)c1ccccc1]

Methylstyrene (2.95 g, 25 mmol), tosyl chloride (4.77 g, mmol), Cu(I)Cl (2.48 g, 25 mmol) and triethylamine (2.53 g, mmol) were placed in 70 ml dry acetonitrile and heated under reflux for 3 h under an argon atmosphere. After drawing off the solvent on a rotary evaporator, the crude product was taken up in 30 ml dichloromethane and washed with 1N HCl (2×20 ml), saturated NaHCO$_3$ solution (ix 20 ml) and saturated NaCl solution (1×20 ml). After purification using column chromatography with dichloromethane as mobile solvent, 1-methyl-4-((2-phenylallyl)sulfonyl)benzene 9 was obtained in a yield of 3.60 g (53% theoretical).

$^1$H-NMR (200 MHz, CDCl$_3$) δ=7.59 (d, J=7.64 Hz, 2H; Ar—H), 7.5-6.9 (m, 7H; Ar—H), 5.51 (s, 1H; C=H$_2$), 5.14 (s, 1H; C=H$_2$), 4.18 (s, 2H; —SO$_2$—CH$_2$—), 2.32 (s, 3H; Ar—CH$_3$) ppm.

Example 14

Synthesis of 2-(tosylmethyl)acrylic acid (10)

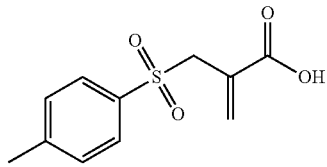 [SMILES: C=C(CS(=O)(=O)c1ccc(C)cc1)C(=O)O]

Bromomethacrylic acid (8.25 g, 50 mmol) was dissolved in 250 ml hot MeOH and NaOH (2 g, 50 mmol) was added to it. Then sodium p-toluenesulfinate (8.91 g, 50 mmol) was added in portions and heated for 2 h under reflux. After drawing off the solvent on a rotary evaporator, the solid residue was taken up in 500 ml water and 2-(tosylmethyl) acrylic acid 10 was precipitated using 1 N HCl. Yield 7.44 g (62% theoretical).

¹H-NMR (200 MHz, CDCl₃) δ=8.81 (bs, 1H), 7.67 (d, J=8.6 Hz, 2H; Ar—H), 7.27 (d, J=8.6 Hz, 2H; Ar—H), 6.55 (s, 1H; C=H₂), 5.94 (s, 1H; C=H₂), 4.04 (s, 2H; —SO₂—CH₂—), 2.36 (s, 3H; Ar—CH₃) ppm.

Example 15

Synthesis of N-methyl-N-propyl-2-(tosylmethyl)acrylamide (11)

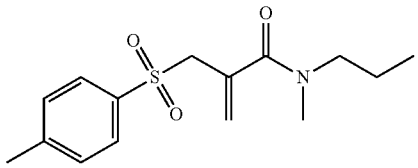 [SMILES: C=C(CS(=O)(=O)c1ccc(C)cc1)C(=O)N(C)CCC]

2-(Tosylmethyl)acrylic acid 10 (3.00 g, 12.5 mmol) was heated under reflux in 30 ml thionyl chloride for 2 h. After drawing off the excess SOCl₂, the acid chloride was taken up in 100 ml dichloromethane and 6 equivalents of propyl methyl amine were slowly added to it at 0° C. After stirring at RT for 12 h, the solvent was drawn off on a rotary evaporator and, after being taken up in 20 ml dichloromethane, the crude product was washed with 1 N HCl (2×20 ml) and saturated NaCl solution (1×20 ml). After purification using column chromatography (PE:EE (1:1)+0.5% acetic acid), 701 mg (19% theoretical)N-methyl-N-propyl-2-(tosylmethyl)acrylamide 11 was obtained.

¹H-NMR (200 MHz, CDCl₃) δ=7.78 (d, J=8.1 Hz, 2H; Ar—H), 7.34 (d, J=8.1 Hz, 2H; Ar—H), 5.51 (bs, 1H; C=H₂), 5.41 (s, 1H; C=H₂), 4.09 (s, 2H; —SO₂—CH₂—), 3.5-2.7 (m, 5H; N—CH₃, N—CH₂—CH₂—CH₃), 2.38 (s, 3H; Ar—CH₃), 1.7-1.3 (m, 2H; N—CH₂—CH₂—CH₃), 0.85 (t, J=7.5 Hz, 3H; N—CH₂—CH₂—CH₃) ppm.

Example 16

Synthesis of 14-methyl-13-oxo-3,6,9,12-tetraoxapentadec-14-en-1-yl 2-(tosylmethyl)acrylate (12)

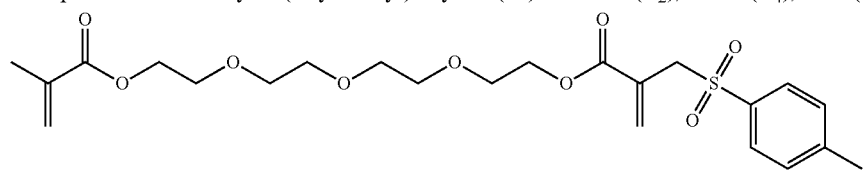

Tetraethylene glycol dimethacrylate (TTEGDMA, 14.6 g, 44.7 mmol) and 4-toluenesulfonyl iodide (12.6 g, 44.7 mmol) were stirred together in CH₂Cl₂ (approx. 100 ml) at room temperature under yellow light. The synthesis took place analogously to the synthesis of Example 2. Triethylamine (22.6 g, 223.4 mmol) was added dropwise (solid precipitated out). The crude product was purified using column chromatography with a mixture of PE/EE 1/3. (R_f~0.38). Yield 24%.

¹H-NMR (200 MHz, CDCl₃, δ): 7.70 (d, J=8.2 Hz, 2H; Ar—H), 7.31 (d, J=8.2 Hz, 2H; Ar—H), 6.49 (s, 1H; =CH₂), 6.10 (m, 1H; =CH₂), 5.86 (s, 1H; =CH₂), 5.50 (m, 1H; =CH₂), 4.27 (m, 2H; —OOC—CH₂—), 4.12 (m, 4H; —OOC—CH₂—, —SO₂—CH₂—), 3.71 (m, 2H; OOC—CH₂—CH₂—), 3.63 (m, 10H; —CH₂—O—CH₂—CH₂—O—CH₂—CH₂—), 2.41 (s, 6H; Ar—CH₃) 1.92 (m, 3H; —CO—C—CH₃).

¹³C-NMR (50 MHz, CDCl₃, δ): 164.9 (C=O), 145.0 (C₄), 136.2 (C₄) 135.5 (C₄), 133.7 (C₂), 129.8 (C₃), 129.0 (C₄), 128.9 (C₃), 125.9 (C₂), 70.7 (C₂), 69.2 (C₂), 68.9 (C₂), 64.6 (C₂), 64.0 (C₂), 57.7 (C₂), 21.8 (C₁), 18.4 (C₁).

Example 17

Synthesis of 2-(methylsulfonylmethyl)-acrylic acid ethyl ester (13)

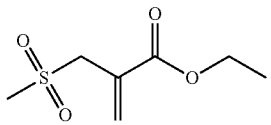

Ethyl 2-(bromomethyl)acrylate (1.1 g, 5.8 mmol), sodium methanesulfinate (0.7 g, 6.7 mmol) and 0.1 g polyethylene oxide 400 were placed in 10 ml absolute THF under an argon atmosphere. Heating then took place under reflux for 20 hours, wherein the progress of the reaction was monitored using NMR and TLC. Once the reaction was complete, the reaction solution was diluted with 10 ml deionized water and 10 ml diethyl ether. The aqueous phase was extracted three times with 25 ml diethyl ether in each case. The combined organic phases were then washed with saturated saline solution, dried over sodium sulfate and evaporated on a rotary evaporator. The crude product obtained was purified using column chromatography with a mixture of PE/EE 1/1. (R_f~0.45). Yield 33%.

¹H-NMR (200 MHz, CDCl₃, δ): 6.64 (s, 1H; =CH₂), 6.15 (s, 1H; =CH₂), 4.28 (q, J=7.1 Hz, 2H; —COO—CH₂—CH₃), 4.06 (s, 2H; —SO₂—CH₂—C—), 2.90 (s, 3H; —SO₂—CH₃), 1.33 (t, J=7.1 Hz, 3H; —COO—CH₂—CH₃).

¹³C-NMR (50 MHz, CDCl₃, δ): 165.3 (C=O), 133.9 (C₂), 129.1 (C₄), 61.9 (C₂), 56.4 (C₂), 40.5 (C₁), 14.1 (C₁).

Example 18

Synthesis of 2-methylene-3-[(4-methylphenyl) sulfonyl]butyric acid methyl ester (14)

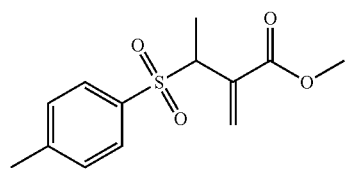

(Z)-Methyl-2-(bromomethyl)but-2-enoate (2.7 g, 14.0 mmol) and 0.5 g polyethylene oxide 400 were placed in 15 ml absolute THF and cooled to −20° C. Sodium p-toluenesulfinate (0.8 g, 4.7 mmol) was then added slowly. Stirring was carried out at −20° C. for 10 hours. Purification was carried out using column chromatography with a mixture of PE/EE 2/1. ($R_f$~0.50). Yield 36%.

$^1$H-NMR (200 MHz, CDCl$_3$, δ): 7.69 (d, J=8.2 Hz, 2H; Ar—H), 7.30 (d, J=8.2 Hz, 2H; Ar—H), 6.53 (s, 1H; =CH$_2$), 5.98 (s, 1H; =CH$_2$), 4.58 (q, J=7.2 Hz, 1H; —SO$_2$—CH—), 3.60 (s, 3H; —COO—CH$_3$), 2.42 (s, 3H; Ar—CH$_3$), 1.54 (d, J=7.2 Hz, 3H; —SO$_2$—CH—C̲H̲$_3$).

Example 19

Preparation and Characterization of Polymers with Dimethacrylates and Transfer Reagents A 1/1 mixture (mol/mol) of UDMA and D$_3$MA (2M) as well as mixtures of UDMA, D$_3$MA and in each case one transfer reagent (compounds nos. 1, 2, 5-14) were prepared according to Table 3. The formulations additionally contained 1 wt.-% Ge initiator (Ivocerin). To check the photoreactivity, the formulations prepared were measured using a photorheometer (MCR 302 WESP model, Anton Paar). A plate-plate measuring system of the PP25 type was used and the measuring gap was set to 0.1 mm. Before and during curing with a UV lamp (Omnicure 2000 model; 400-500 nm; 1 W/cm$^2$ and 3 W/cm$^2$ respectively), the storage modulus and loss modulus of the sample were measured in the oscillation mode (1% deflection, 1 Hz).

The double-bond conversion (DBC) achieved at the gel point (intersection of the storage modulus and the loss modulus) serves as a measure of the polymerization shrinkage occurring. The double-bond conversion at the gel point does not lead to the build-up of stresses as the polymerization shrinkage occurring is compensated for by flow processes. The higher the double-bond conversion is at the gel point, the lower are consequently the double-bond conversion and the polymerization shrinkage in the gel condition, which thus also leads to a lower polymerization shrinkage force. To determine the glass transition, the formulations were poured into silicone moulds and polymerized in a light furnace (Lumamat 100 model, Ivoclar AG) using program 2 (P2: 10 min irradiation with an intensity of approx. 20 mW/cm$^2$). The rods were turned and cured again using P2. The test rods were ground and then measured on a rheometer (MCR 302 model) with a CTD oven (Convection Temperature Control) and an installed solid-clamping device (SRF12 for rectangular cross-sections up to 12 mm). The heating rate set was 2° C./min. All samples were heated from −100° C. to 200° C. and oscillated at a constant frequency of 1 Hz and 0.1% deflection.

The glass transition temperatures shown in Table 3 (maxima of the loss modulus graphs) show that the addition of the transfer reagents leads to a deeper and significantly narrower glass transition range, which makes debonding-on-demand substantially easier in the compositions according to the invention. Moreover, it can be seen that the double-bond conversion at the gel point is increased by the transfer reagents. A lower shrinkage stress is therefore to be expected because stresses can be dissipated by flow processes up to the gel point.

TABLE 3

| Formulation | $T_G$ [° C.] | HW [° C.] | DBC [%] |
|---|---|---|---|
| 2M$^{a)}$* | 150 | 152 | 18 |
| 2M$^{c)}$* | 148 | 145 | 18 |
| 2M + 35 wt.-% 1 | 50 | 28 | $^{b)}$ |
| 2M + 29 wt.-% 2 | 75 | 32 | 23 |
| 2M + 29 wt.-% 5 | 48 | 51 | 30 |
| 2M + 14 wt.-% 6 | 134 | 51 | 24 |
| 2M + 16 wt.-% 7 | 68 | 51 | 29 |
| 2M + 6 wt.-% 8$^{c)}$ | 129 | 93 | 51 |
| 2M + 7 wt.-% 9$^{c)}$ | 126 | 82 | 28 |
| 2M + 6 wt.-% 10$^{c)}$ | 114 | 55 | 25 |
| 2M + 34 wt.-% 11$^{c)}$ | 74 | 57 | 36 |
| 2M + 45 wt.-% 12 | 64 | 23 | $^{b)}$ |
| 2M + 20 wt.-% 13 | 66 | 26 | $^{b)}$ |
| 2M + 26 wt.-% 14 | 65 | 74 | $^{b)}$ |

*Comparison example
$T_G$ Glass transition temperature
HW Half width
DBC Double-bond conversion at the gel point
$^{a)}$2M: UDMA/D$_3$MA (1/1)
$^{b)}$ Not measured
$^{c)}$Curing with 3 W/cm$^2$

The invention claimed is:

1. Radically polymerizable dental material, which contains at least one radically polymerizable monomer, at least one initiator for the radical polymerization and at least one compound of Formula I:

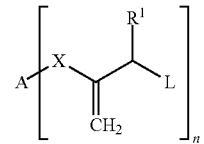

wherein the variables of Formula I have the following meanings:
A a saturated, linear aliphatic hydrocarbon residue with 1 to 12 carbon atoms which can be interrupted by one or more 1,4-phenylene groups, urethane groups or O and which can carry in the terminal position a polymerizable methacryloyloxy group,
X —COO— or —CON(R$^{10}$)—, wherein R$^{10}$ is methyl, or is absent, wherein the bond to A takes place via O or N;
R$^1$ H,
L SO$_2$R$^3$, wherein R$^3$ is CH$_3$ or tolyl,
n 1 or 2.

2. Dental material according to claim 1, wherein the variables of Formula I have the following meanings:
A a saturated, linear aliphatic hydrocarbon radical with 6 to 12 carbon atoms which can be interrupted by 1 to 3 O atoms,
X —COO—,
R$^1$ H,
L SO$_2$R$^3$, wherein R$^3$ is CH$_3$ or tolyl, n 1 or 2.

3. Dental material according to claim 1, which contains at least one multifunctional (meth)acrylate or a mixtures of mono- and multifunctional (meth)acrylates.

4. Dental material according to claim 1, which contains at least one filler.

5. Dental material according to claim 1, which additionally contains at least one photoinitiator for the radical polymerization.

6. Dental material according to claim 1, which contains 0.5 to 60 wt.-% of at least one compound of general formula I, 0.01 to 5.0 wt.-% initiator(s) for the radical polymerization, and optionally 5 to 80 wt.-% multifunctional (meth)acrylate(s), in each case relative to the total mass of the dental material.

7. Dental material according to claim 6, which has the following composition:
   (a) 5 to 80 wt.-% multifunctional (meth)acrylate(s),
   (b) 0.01 to 5.0 wt.-% initiator(s),
   (c) 0.5 to 60 wt.-% of at least one compound of general formula I,
   (d) 0 to 50 wt.-% monofunctional (meth)acrylate(s),
   (e) 0 to 90 wt.-% filler(s), and
   (f) 0 to 5 wt.-% additive(s),
   in each case relative to the total mass of the dental material.

8. Dental material according to claim 1, which does not contain volatile mercaptans.

9. Dental material according to claim 8 for intraoral use to restore damaged teeth.

10. Dental material according to claim 9 for use as cement, filling composite or veneering material.

11. Method of using the dental material according to claim 1 comprising extraorally manufacturing or repairing dental restorations.

12. Method of using the dental material according to claim 11 wherein the dental restorations comprise inlays, onlays, crowns or bridges.

13. Method of using the compound of Formula (I), comprising defining the variables in claim 1 to reduce the polymerization shrinkage stress of dental materials.

14. Dental material according to claim 1, which contains
   1.0 to 50 wt.-% of at least one compound of general formula I,
   0.1 to 5.0 wt.-% initiator(s) for the radical polymerization, and optionally
   10 to 70 wt.-% multifunctional (meth)acrylate(s), in each case relative to the total mass of the dental material.

15. Dental material according to claim 1, which contains
   1.0 to 40 wt.-% of at least one compound of general formula I,
   0.1 to 3.0 wt.-% initiator(s) for the radical polymerization, and optionally
   10 to 60 wt.-% multifunctional (meth)acrylate(s), in each case relative to the total mass of the dental material.

16. Dental material according to claim 6, which comprises:
   (a) 10 to 70 wt.-% multifunctional (meth)acrylate(s),
   (b) 0.1 to 5.0 wt.-% initiator(s),
   (c) 1.0 to 50 wt.-% of at least one compound of general formula I,
   (d) 0 to 40 wt.-% monofunctional (meth)acrylate(s),
   (e) 5 to 90 wt.-% filler(s), and
   (f) 0 to 3 wt.-% additive(s),
   in each case relative to the total mass of the dental material.

17. Dental material according to claim 6, which comprises:
   (a) 10 to 60 wt.-% multifunctional (meth)acrylate(s),
   (b) 0.1 to 3.0 wt.-% initiator(s),
   (c) 1.0 to 40 wt.-% of at least one compound of general formula I,
   (d) 0 to 30 wt.-% monofunctional (meth)acrylate(s),
   (e) 0 to 80 wt.-% filler(s), and
   (f) 0.2 to 3 wt.-% additive(s),
   in each case relative to the total mass of the dental material.

18. Dental material according to claim 1, which does not contain any mercaptans at all.

19. Dental material according to claim 1, which does not contain other sulphur compounds.

* * * * *